May 26, 1942. W. E. LAMMERTS Plant Pat. 522
ROSE PLANT
Filed Nov. 24, 1941
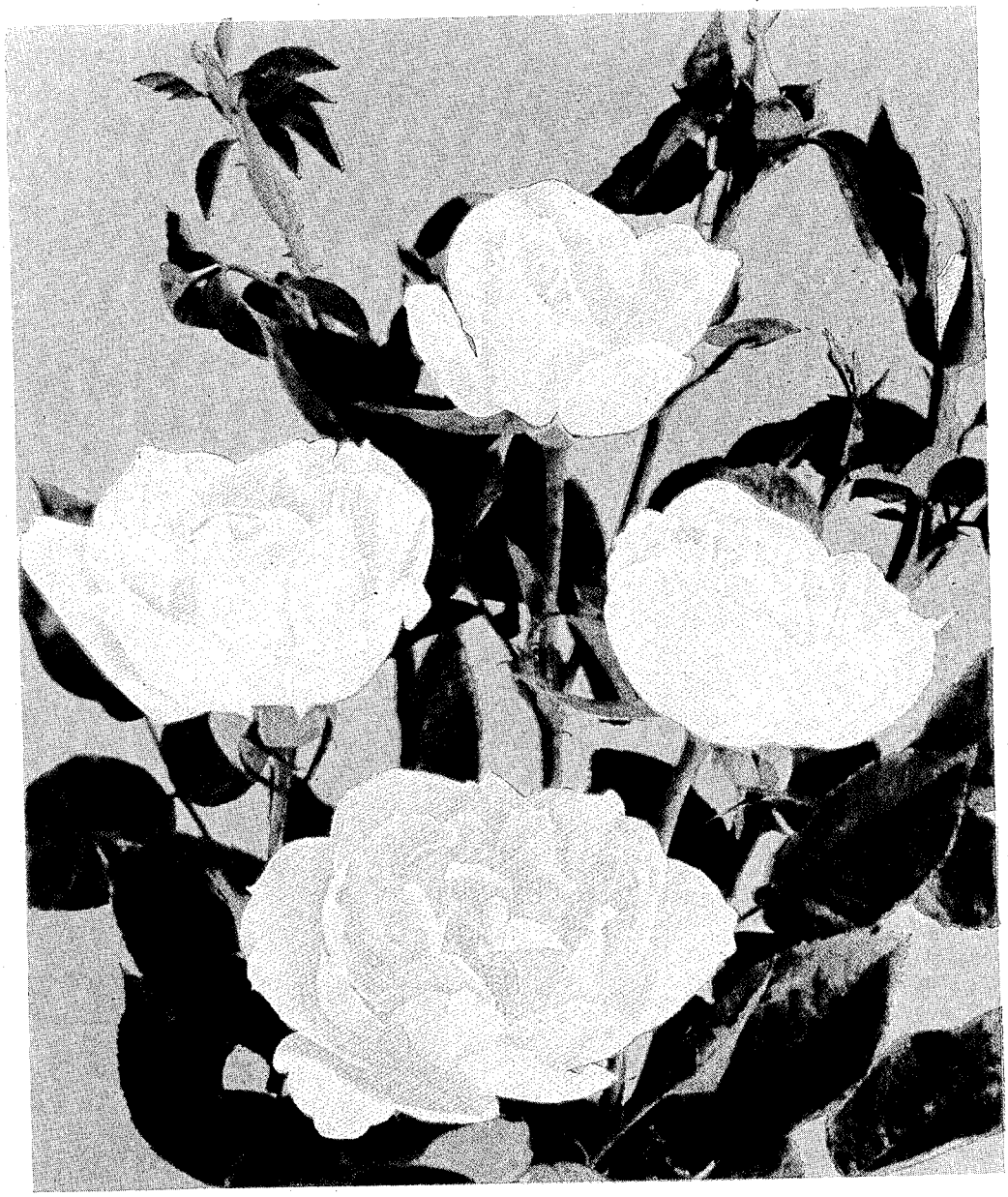
Inventor
W. E. Lammerts
By Robb & Robb
Attorneys Patented May 26, 1942

Plant Pat. 522

UNITED STATES PATENT OFFICE

522

ROSE PLANT

Walter E. Lammerts, Ontario, Calif., assignor to Armstrong Nurseries, Inc., Ontario, Calif., a corporation of California Application November 24, 1941, Serial No. 420,305

1 Claim. (Cl. 47—61)

The present invention relates to a new and distinct variety of rose plant, the result of a definite effort to obtain by the use of two well-known varieties each having certain well defined and desirable characteristics, a hybrid which would combine these desirable features while eliminating certain disadvantageous characteristics of the parent plants.

More specifically speaking, one of the objects of my breeding program was to obtain a rose similar in color to the seed parent employed, "Angele Pernet," but having the vigor characterizing the pollen parent used, "President Herbert Hoover." This objective was definitely attained and along with it, the new variety was found to exhibit other important distinctions, giving rise to a markedly improved rose unlike any heretofore existing so far as I am aware.

As above premised, this new variety has the vigor of growth of its pollen parent, and, in addition, is characterized by a very strong and pleasant spicy and penetrating fragrance somewhat like that of attar of roses.

The stems of the plant are more nearly like those of the seed parent in size and length, and the petals of the flowers are shaped more like that of "Angele Pernet." Also the gloss of the foliage is similar to that of the seed parent. However, the number of petals of the flowers in this new variety is greater than found in either of its parents.

Perhaps the most distinctive features of the present rose are the extremely high and unusual fragrance and the fact that the border of each petal is margined with a "pencil-line" varying in color from near Sea Foam Yellow to near Lemon Chrome in the newly opened flower.

This new variety is more resistant to mildew than is "President Herbert Hoover" and similar to "Angele Pernet" in this respect while the floriferousness of the plant is comparable to that of "President Herbert Hoover."

Other features of distinction are set forth in the following detail description, wherein all references to color accord with Ridgway's Color Standard:

Type: Bush; for cut flowers and garden decoration.

Class: Hybrid Tea.

Breeding: Seedling.

*Seed parent.*—Angele Pernet.

*Pollen parent.*—President Herbert Hoover.

Propagation: Holds its distinguishing characteristics through succeeding propagations by budding.

*Flower*

Locality where grown: Ontario, California.

Flowers borne: Usually singly, sometimes several to stem; in irregular cluster, on strong, long stems.

Quantity of bloom: Abundant outdoors.

Continuity: Almost continuous during growing season.

Fragrance: Penetrating, strong; spicy like attar of Roses.

Bud:

*Pedicel.*—Medium long; moderately heavy; erect; stiff; smooth; few gland-tipped cilia near Calliste Green, Plate VI.

*Before calyx breaks.—Size—medium. Form*—long, pointed, with foliaceous appendages, gland-tipped cilia slightly hairy on the surface of the bud; with slender, much-cut foliaceous parts extending beyond the tip of the bud equal to one-half or more of its length.

*As calyx breaks.*—Outside of petal—near Pinkish Cinnamon, Plate XXIX, with shadings of near Orange Cinnamon, Plate XXIX, blending gradually to between Chalcedony Yellow, Plate XVII, and Clear Dull Green Yellow, Plate XVII, at base of petal. Inner surface of sepal with fine, woolly tomentum; both margins of one sepal lined with woolly tomentum; margins of another sepal lined on one side with woolly tomentum, and on the other margin with stipitate glands. Both margins of the three other sepals are lined with stipitate glands.

*As first petal opens.—Size—medium. Form*—ovoid. *Color—outside—near Begonia Rose,* Plate I, at tip of petal blending gradually to between Bittersweet Orange, Plate II, and Salmon Orange, Plate II, blending abruptly, at point of attachment, to between Lemon Chrome, Plate IV, and Lemon Yellow, Plate IV. Border of petal margined with pencil-line of near Sea Foam Yellow, Plate XXXI. Inside—near Begonia Rose, Plate I, at tip, blending gradually to near Salmon Orange, Plate II, at base. Point of attachment near Lemon Chrome, Plate IV. Border of petal margined with pencil-line of near Sea Foam Yellow, Plate XXXI. *Opening*—opens up well.

Bloom:

*Size, when fully open.*—Medium to moderately large; approximately 3½ inches to 4 inches.

*Petalage.*—Double, from 32 to 38 petals; arranged irregularly.

*Form.*—High center at first, becoming very flat; petals remaining at first loosely, but sometimes tightly, rolled outward; becoming later, at maturity, nearly flat, loosely rolled outward, and most petals have a mucronate tip.

Petals: Medium thick, with inside velvety and outside satiny.

*Shape.*—Outside—broadly obovate, sometimes mucronate; sometimes scalloped with one or more notches. Intermediate—obovate, usually mucronate; usually scalloped with one or more notches. Inside—obovate, mucronate; slightly scalloped with few, if any, notches.

*Color.*—Colors modified by being bordered and shaded with other colors.

This description of a newly opened flower was made from a rose grown outdoors in the month of August, 1941, at Ontario, California:

*Color.*—Outside petal: outside surface—between Hermosa Pink, Plate I, and Chatenay Pink, Plate XIII, at tip, blending gradually to between Bittersweet Orange, Plate II, and Bittersweet Pink, Plate II, at base. Point of attachment marked near Lemon Yellow, Plate IV. Border of petal margined with pencil-line of near Sea Foam Yellow, Plate XXXI; inside surface—near Thulite Pink, Plate XXVI, at tip, blending gradually to between near Bittersweet Orange, Plate II, and near Bittersweet Pink, Plate II, at base. Point of attachment marked near Lemon Chrome, Plate IV. Border of petal margined with pencil-line of near Sea Foam Yellow, Plate XXXI. Intermediate petal: outside surface—near Geranium Pink, Plate I, at tip blending gradually to near Bittersweet Pink, Plate II, at base and marked near Lemon Yellow, Plate IV, at point of attachment. Border of petal margined with pencil-line of near Sea Foam Yellow, Plate XXXI, at tip blending gradually on both sides to near Pale Lemon Yellow, Plate IV, at base of petal; inside surface—near Begonia Rose, Plate I, at tip blending gradually to between Bittersweet Orange, Plate II, and Bittersweet Pink, Plate II, which in turn blends rather abruptly to near Lemon Chrome, Plate IV, at point of attachment. Border of petal margined with pencil-line of near Sea Foam Yellow, Plate XXXI, at tip blending gradually on both sides to near Lemon Yellow, Plate IV, at base of petal. Inner petal: outside surface—between Rose Doree, Plate I, and Geranium Pink, Plate I, at tip blending gradually to between Bittersweet Orange, Plate II, and Bittersweet Pink, Plate II, at base which in turn blends into near Lemon Yellow, Plate IV, at point of attachment. Border of petal margined with pencil-line of near Sea Foam Yellow, Plate XXXI, at tip blending gradually on both sides to near Empire Yellow, Plate IV, at base; inside surface—near Begonia Rose, Plate I, at tip blending gradually to near Salmon Orange, Plate II, at base of petal which in turn blends rather abruptly to near Lemon Chrome, Plate IV, at point of attachment. Border of petal margined with pencil-line of near Sea Foam Yellow, Plate XXXI, at tip blending gradually on both sides to near Lemon Chrome, Plate IV, at base of petal.

This description was made from a rose that was open for three days indoors in the month of August, 1941, at Ontario, California:

*Color.*—Outside petal: outside surface—upper half of petal near Hermosa Pink, Plate I, blending and shading very gradually to near Bittersweet Pink, Plate II, toward base of petal, changing abruptly first to Sulphur Yellow, Plate V, and then to Lemon Yellow, Plate IV, at point of attachment. Close observation reveals a very fine pencil-line margin around border of petal of between White and Hermosa Pink, Plate I, at tip margin blending gradually to near Maize Yellow, Plate IV, on both side margins and finally blending gradually to near Picric Yellow, Plate IV, at base; inside surface—near Thulite Pink, Plate XXVI, and maintaining near Thulite Pink toward the base of petal where it blends gradually to a faint near Salmon-Buff, Plate XIV, when in turn changes abruptly to near Lemon Yellow, Plate IV, at point of attachment. Pencil-line margin around upper half of petal between White and near Maize Yellow, Plate IV, blending gradually on both sides to near Lemon Yellow, Plate IV, at base. Inside petal: outside surface—upper half of petal between Hermosa Pink, Plate I, and Eosine Pink, Plate I, blending gradually to near Orange Pink, Plate II, and then to near Straw Yellow, Plate XVI, toward the base of petal changing abruptly at point of attachment to near Lemon Yellow, Plate IV. Pencil-line margin around upper half of petal between White and near Maize Yellow, Plate IV, blending gradually on both sides to near Lemon Yellow, Plate IV, at base; inside surface—upper half of petal between Thulite Pink, Plate XXVI, and Eosine Pink, Plate I, blending gradually to a faint shading of near Bittersweet Pink, Plate II, toward base of petal then changing abruptly to near Lemon Yellow, Plate IV, at point of attachment. Pencil-line margin around upper half of petal between White and near Maize Yellow, Plate IV, blending gradually on both sides to near Lemon Yellow, Plate IV, at base.

*General color effect.*—Newly opened flower—center near Rose Doree, Plate I. Outer petals—between Hermosa Pink, Plate I, and La France Pink, Plate I. Three days open—outside petals near Hermosa Pink, Plate I, and the inside petals near Eosine Pink, Plate I.

*Behavior.*—Drop off cleanly; fading lighter in hot, dry weather.

*Flower longevity.*—On bush in garden three days in August; cut flowers grown outdoors kept at living room temperatures three to four days in August.

*Reproductive organs*

Stamens: Medium to many; arranged irregularly about pistils, mixed with petaloids.

Filaments: Medium length; near Lemon Chrome, Plate IV: mostly with anthers.

Anthers: Small to medium; open at various times; near Capucine Yellow, Plate III.

Pollen: Moderately abundant; between Capucine Yellow, Plate III, and Deep Chrome, Plate III.
Pistils: Medium number.
Styles: Uneven; medium length; thin to medium; loosely bunched.
Stigma: Between Chalcedony Yellow, Plate XVII, and Clear Dull Green Yellow, Plate XVII.
Ovaries: Some protruding from calyx.
Hips: Short; depresso-globose with inconspicuous neck. *Mature hip*—near Van Dyke Brown, Plate XXVIII. This hip was not fully mature and was partly colored with near Deep Chrysolite Green, Plate XXXI; moderately smooth—under strong magnifying glass a fine fuzzy bloom may be seen; walls medium thick, fleshy.
Sepals: Permanent; moderately long; recurved. *Color.*—Inside—near Light Dull Green Yellow, Plate XVII, at base blending quickly to near Light Grape Green, Plate XLI, toward tip of sepal. Blendings of white woolly tomentum are most prominent toward tip of sepal. Outside—near Rainette Green, Plate XXXI, with blendings of near Parrot Green, Plate VI, which in turn blend into near Calliste Green, Plate VI, at base of sepal.
Seed: Few; medium size.

*Plant*

Foliage:

*Leaves.*—Pinnate; compound of three to five, and sometimes seven, leaflets; moderately abundant; medium to large; moderately heavy, leathery, glossy.

*Leaflets.*—*Shape*—ovate to ovate-cuspidate with apex acute to mucronate, base round; margin simply sometimes irregularly serrate.

*Color.*—Mature—upper surface—near Yew Green, Plate XXXI. Under surface—between Rainette Green, Plate XXXI, and Deep Chrysolite Green, Plate XXXI, much veined with near Light Cress Green, Plate XXXI. Young—upper surface—near Mars Violet, Plate XXXVIII, at margin usually blending gradually to between Hellebore Green, Plate XVII, and Elm Green, Plate XVII. Under surface—a blending of near Neutral Red, Plate XXXVIII, and near Rainette Green, Plate XXXI, with shadings of Neutral Red, Plate XXXVIII, predominating.

*Rachis.*—Medium heavy. Upper side—grooved, hairy and glandular. Under side—moderately smooth; few prickles.

*Stipules.*—Medium length; medium wide; with medium long points turning out at an angle of more or some slightly less than 45°, recurved toward the stem and some slightly recurved away from stem.

*Disease.*—Moderately resistant to mildew.

Growth:

*Habit.*—Bushy; upright; much branched.

*Growth.*—Vigorous.

*Canes.*—Moderately heavy.

*Main stems.*—*Color*—between near Light Cress Green, Plate XXXI, and near Rainette Green, Plate XXXI. *Large prickles*—many; medium long; some straight, and some slanting slightly downward with long, narrow base. *Color*—usually between Snuff Brown, Plate XXIX, and Bister, Plate XXIX, blending gradually to near Blackish Brown (2), Plate XLV, at point or tip. Colors and shadings slightly variable even on the same stem. *Small prickles*—several. *Color*—usually between Snuff Brown, Plate XXIX, and Bister, Plate XXIX, blending gradually to near Blackish Brown (2), Plate XLV, at point or tip. Colors and shadings slightly variable even on the same stem. *Hairs*—none, but a fuzzy bloom may be seen under magnifying glass.

*Branches.*—Side exposed to most sun near Rainette Green, Plate XXXI. Side exposed to less sun near Light Cress Green, Plate XXXI. *Large prickles*—many; medium long; some straight; mostly slanting downward, with usually long, narrow base. *Color*—large prickles on the branches are variable as to colors and blendings. Some are near Verona Brown, Plate XXIX, some are near Straw Yellow, Plate XVI, tipped with near Hessian Brown, Plate XIII. However, prickles having near Acajou Red, Plate XIII, at base blending gradually into near Lime Green, Plate XXXI, at tip seem to be most common. *Small prickles*—several, having same characteristics as noted above in respect to the large prickles. Hairs—none.

*New shoots.*—*Color*—near Courge Green, Plate XVII. Side exposed to most sun is near Rainette Green, Plate XXXI. *Large prickles*—many; medium long; mostly straight; some slanting slightly downward, usually with long, narrow base. *Color*—usually near Deep Corinthian Red, Plate XXVII, at base blending gradually to near Lime Green, Plate XXXI, at tip or point. *Small prickles*—many. *Color*—usually near Deep Corinthian Red, Plate XXVII, at base blending gradually to near Lime Green, Plate XXXI, at tip or point. *Hairs*—none, but under magnifying glass a fuzzy bloom may be seen.

I claim:

A new and distinct variety of rose plant, characterized as to novelty by its vigor of growth, the extremely high and unusual fragrance of its flowers, color combination of said flowers, number of petals thereof, and disease resistance of the plant, substantially as shown and described.

WALTER E. LAMMERTS.